(12) United States Patent
Reiterer et al.

(10) Patent No.: US 11,969,155 B2
(45) Date of Patent: Apr. 30, 2024

(54) ELECTROSURGICAL INSTRUMENT, ELECTROSURGICAL DEVICE AND METHOD FOR OPERATING AN ELECTROSURGICAL DEVICE

(71) Applicant: Erbe Elektromedizin GmbH, Tuebingen (DE)

(72) Inventors: Markus Reiterer, Loipersbach (AT); Achim Brodbeck, Metzingen (DE); Klaus Fischer, Nagold (DE); Marc Mueller, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 89 days.

(21) Appl. No.: 17/498,351

(22) Filed: Oct. 11, 2021

(65) Prior Publication Data
US 2022/0117478 A1 Apr. 21, 2022

(30) Foreign Application Priority Data
Oct. 19, 2020 (EP) ...................................... 20202483

(51) Int. Cl.
| | |
|---|---|
| *A61B 1/12* | (2006.01) |
| *A61B 1/00* | (2006.01) |
| *A61B 1/005* | (2006.01) |
| *A61B 1/015* | (2006.01) |
| *A61B 1/07* | (2006.01) |
| *A61B 1/313* | (2006.01) |

(Continued)

(52) U.S. Cl.
CPC .......... *A61B 1/126* (2013.01); *A61B 1/00119* (2013.01); *A61B 1/005* (2013.01); *A61B 1/015* (2013.01); *A61B 1/07* (2013.01); *A61B 1/3132* (2013.01); *A61B 18/1482* (2013.01); *A61B 2018/00589* (2013.01); *A61B 2018/00601* (2013.01)

(58) Field of Classification Search
CPC ..... A61B 1/126; A61B 1/00119; A61B 1/005; A61B 1/015; A61B 1/07; A61B 1/3132; A61B 18/1482; A61B 2018/00589; A61B 2018/00601
USPC .......................................................... 606/13
See application file for complete search history.

(56) References Cited

U.S. PATENT DOCUMENTS

| | | | |
|---|---|---|---|
| 5,435,805 | A | 7/1995 | Edwards et al. |
| 10,154,786 | B2 | 12/2018 | Fischer et al. |

(Continued)

FOREIGN PATENT DOCUMENTS

| | | |
|---|---|---|
| EP | 2 815 713 A1 | 12/2014 |
| EP | 3 517 028 A1 | 7/2019 |
| EP | 3 545 888 A1 | 10/2019 |

*Primary Examiner* — Aaron F Roane
(74) *Attorney, Agent, or Firm* — Blank Rome LLP

(57) ABSTRACT

An electrosurgical instrument configured for connection to a supply apparatus for operation. The instrument has an end opening at the distal end and supports at least one electrode in the area of the end opening to which an alternating voltage potential can be applied. Directly adjoining the end opening, a liner of the electrosurgical instrument limits a flow chamber inside the liner. With distance to the end opening a flushing channel opens out into the flow chamber via an exit opening and a suction channel opens out into the flow chamber via an inlet opening. A flushing fluid can be introduced in the flow chamber via the flushing channel and can be extracted by suction via the suction channel.

14 Claims, 3 Drawing Sheets

(51) Int. Cl.
*A61B 18/14* (2006.01)
*A61B 18/00* (2006.01)

(56) References Cited

U.S. PATENT DOCUMENTS

| | | |
|---|---|---|
| 10,251,695 B2 | 4/2019 | Fischer et al. |
| 2012/0289954 A1 | 11/2012 | Lam |
| 2012/0303016 A1 | 11/2012 | Fischer et al. |
| 2017/0325886 A1* | 11/2017 | Graham ............. A61B 18/1482 |

* cited by examiner

ELECTROSURGICAL INSTRUMENT, ELECTROSURGICAL DEVICE AND METHOD FOR OPERATING AN ELECTROSURGICAL DEVICE

CROSS-REFERENCE TO RELATED APPLICATION

This application claims priority to European Application No. 20202483.2, filed Oct. 19, 2020, the entirety of which is incorporated by reference herein.

TECHNICAL FIELD

Embodiments of the invention refer to an electrosurgical instrument that can be supplied by means of a supply apparatus, particularly with electrical energy and a flushing fluid. In addition, the supply apparatus can comprise further devices or units that can be connected electrically and/or fluidically and/or optically with the instrument. Embodiments of the invention also refer to an electrosurgical device comprising an electrosurgical instrument that is connected to a supply apparatus as well as a method for operating such an electrosurgical device.

BACKGROUND

EP 2 815 713 A1 describes an electrosurgical instrument comprising a light conducting device as well as at least one electrode. Biological tissue can be treated by means of the electrode, e.g. for cutting or coagulating of tissue. The light created due to the spark formation between electrode and tissue can be captured by means of a light inlet window and can be transmitted via the light conducting device to a light analysis unit. Based on the light analysis the type of tissue can be determined that is treated by means of the at least one electrode. For capturing light a fluid body is formed on the instrument. This fluid body can be renewed by means of a fluid channel and fluid exit openings at the distal end during operation of the instrument.

A similar electrosurgical instrument is described in EP 3 517 028 A1.

SUMMARY

It can be considered as object of the embodiments of the present invention to provide an electrosurgical instrument that comprises an improved protection against contamination of a light inlet surface of a light conducting device.

This object is solved by means of an electrosurgical instrument having the features of claim 1, an electrosurgical device having the features of claim 10 as well as a method having the features of claim 14.

The electrosurgical instrument according to an embodiment of the invention can be configured for open surgical or laparoscopic application. The electrosurgical instrument has a connection device for connection with a supply apparatus. By means of the connection device an electrical, optical and fluidical connection can be established between the electrosurgical instrument and the supply apparatus. For example, the connection device can comprise one or more plugs or other suitable connection elements by means of which a particularly releasable connection can be established between the supply apparatus and the electrosurgical instrument. The electrical connection, the optical connection and the fluidical connection can thereby be established by one or more common or individual plugs or other suitable connection elements.

The electrosurgical instrument comprises in addition a liner having an end opening at the distal end of a liner. In an embodiment the liner can be formed by a housing or a part of the housing, e.g. in a configuration for the open surgical use. A part of the housing can serve as handle or can comprise a handle. In addition, one or more operation elements for manual actuation can be provided on the housing.

It is also possible to form the liner by a flexible hose, a rigid tube or a combination of flexible hose and rigid tube sections, e.g. in an electrosurgical instrument for the laparoscopic use in combination with an endoscope or for the use with a flexible endoscope. Depending on the configuration, the liner can thus be—at least in sections—rigid or flexible. For example, the liner can consist of plastic and/or a metal alloy.

The connection device can be arranged at a proximal end of the liner. The connection device can comprise one or more lines and/or one or more plugs or similar connection elements.

The instrument has at least one electrode at its distal end. The at least one electrode is electrically connected with the connection device and can thus be connected via the connection device with the supply apparatus. Depending on the embodiment, the at least one electrode is arranged adjacent to an end opening of the liner or extends in a longitudinal direction beyond the end opening, wherein the at least one electrode can extend through the end opening. The longitudinal direction is the direction in which the instrument extends at least adjacent to the end opening of the liner and/or the direction in which the at least one electrode extends adjacent to its distal end. In one embodiment a plane in which the end opening extends can be orientated orthogonal to the longitudinal direction.

The electrosurgical instrument can be configured as monopolar or as bipolar or as multi-polar instrument. In the configuration as monopolar instrument one single electrode on the instrument is sufficient. An additional electrode that can be denoted as counter electrode can be configured separately from the electrosurgical instrument and can be connected with the supply apparatus. If the electrosurgical instrument is configured as bipolar instrument, at least two electrodes are present between which a voltage can be applied during operation.

The electrosurgical instrument has in addition a light conducting device that is optically connected with the connection device. At its distal end the light conducting device comprises a light inlet surface that is arranged inside the liner and that is substantially orientated toward the end opening and/or toward the at least one electrode. The light inlet surface is arranged and orientated such that light created during spark formation at the at least one electrode can incident through the light inlet surface and can be further transmitted optically via the light conducting device toward the connection device. The captured light can be further transmitted via the connection device to the supply apparatus and can be analyzed there, for example in a light analysis unit. If the light analysis unit is part of the electrosurgical instrument in an embodiment, the light conducting device is directly connected with the light analysis unit and an optical connection with the connection device can be omitted.

The electrosurgical instrument further comprises a flushing channel that is fluidically connected with the connection device and that preferably extends inside the liner. The flushing channel has an exit opening at its distal end that opens out into a flow chamber limited by the liner. The exit opening is arranged with distance to the end opening in longitudinal direction. At the opposite in longitudinal direction the end opening of the liner opens out into the flow chamber. With view in longitudinal direction the flow chamber is thus arranged between the exit opening and the end opening. Flushing fluid flowing out of the exit opening forms a flushing fluid flow in the flow chamber. Preferably the flushing fluid flow is at least substantially directed away from the exit opening toward the end opening. By means of the flushing fluid flow in the flow chamber, entering of contaminations that could contaminate the light inlet surface are avoided or at least reduced.

The electrosurgical instrument comprises in addition a suction channel that is fluidically connected with the connection device and that is preferably arranged inside the liner. The suction channel has an inlet opening that opens out into the flow chamber. Via the inlet opening and the suction channel at least a portion of the flushing fluid can be discharged from the flow chamber. Preferably the suction channel is dimensioned such that substantially all of the flushing fluid can be discharged from the flow chamber before flushing fluid exits from the flow chamber via the end opening.

Thus, for example, the amount of flushing fluid can be adjusted that exits from the end opening and impinges on the biological tissue to be treated. The major portion of the flushing fluid entering the flow chamber or all of the flushing fluid entering the flow chamber can be discharged via the suction channel before the flushing fluid exits from the end opening. It has shown that the contamination of the optic and particularly the light inlet opening of the light conducting device can be remarkably reduced thereby, which results in an improved analysis of the actually treated biological tissue. The volume flow rate of the flushing fluid can be remarkably increased compared with former instruments and is preferably greater than 1 l/min and can have an amount of up to 8 l/min, for example.

It is possible to provide multiple suction channels having one inlet opening in each case. In addition or as an alternative, it is also possible to provide multiple flushing channels having one exit opening in each case.

In an embodiment the exit opening of the flushing channel or the section of the flushing channel adjoining the exit opening is orientated such that the main flow direction enters into the flow chamber parallel to the longitudinal direction or inclined by an acute angle with regard to the longitudinal direction. The main flow direction can be defined by the center axis that is orientated orthogonal to the plane of the exit opening.

The inlet opening of the suction channel is preferably arranged with distance to the end opening in longitudinal direction. It is advantageous, if the inlet opening of the suction channel is arranged closer to the end opening in longitudinal direction than the exit opening of the flushing channel. Alternatively, the inlet opening and the exit opening can have equal distances to the end opening in longitudinal direction. In this configuration it is possible that the inlet opening and the exit opening are arranged in a common plane.

As already explained, it can be advantageous, if the electrosurgical instrument is dimensioned or operated such that no flushing fluid of the flushing fluid flow exits from the flow chamber through the end opening. For example, this can be achieved in that the volume flow rate of the flushing fluid through the flushing channel is at most as large as the volume flow rate of the flow through the suction channel. In addition, also the geometry of the flow chamber and/or the arrangement and orientation of the exit opening of the flushing channel and/or the arrangement and orientation of the inlet opening of the suction channel and/or the flow direction of the flushing fluid flow in the flow chamber can be selected such that entering of the flushing fluid in the suction channel is simplified. For example, the flow chamber can taper toward the end opening. In addition or as an alternative, the exit opening and the inlet opening can be arranged and orientated such that the flushing fluid flow comprises a flow direction component from the exit opening toward the inlet opening.

It is also advantageous, if the light inlet surface of the light conducting device has a larger distance from the end opening in longitudinal direction than the exit opening of the flushing channel. In doing so, the protection of the light inlet surface can be further improved.

In an embodiment the light inlet surface or the distal end section of the light conducting device adjoining the light inlet surface can be arranged inside the flushing channel and/or can be arranged directly adjacent to the exit opening, such that the light inlet surface or the adjoining distal end section of the light conducting device is surrounded by flow of flushing fluid, particularly before the flushing fluid leaves through the exit opening. Also by means of this measure an improved protection effect against contamination of the light inlet surface is achieved.

It can be advantageous, if at least one sensor electrically connected with the connection device is provided next to the suction channel. By means of the at least one sensor, a parameter of the flow or the fluid inside the suction channel can be detected, as for example, a pressure, a volume flow rate, a flow velocity or another physical parameter or an arbitrary combination of multiple of the listed parameters.

An electrosurgical device according to an embodiment of the invention comprises an electrosurgical instrument that corresponds to one of the embodiments described above. By means of the connection device, the electrosurgical instrument is connected with a supply apparatus. A light analysis unit is optically connected with the light conducting device or the light inlet surface and is configured to carry out an analysis of the captured light, particularly a spectral analysis. The light analysis unit can be part of the electrosurgical instrument or the supply apparatus or can be configured separately thereto. If the light analysis unit is not part of the electrosurgical instrument, the light analysis unit is optically connected with the connection device such that light can be transmitted via the connection device to the light analysis unit.

The supply apparatus has a voltage source that is electrically connected with the at least one electrode of the electrosurgical instrument. In doing so, an electrical voltage potential, particularly a radio frequency alternating voltage potential can be applied to the at least one electrode.

In addition, the supply apparatus comprises a flushing fluid source that is fluidically connected with the flushing channel as well as a suction unit that is fluidically connected with the suction channel. By means of the flushing fluid source, flushing fluid can be supplied to the flushing fluid channel and thus a flushing fluid flow can be created. By means of the suction unit, a suction flow can be created through the suction channel in order to at least discharge a portion of the flushing fluid or all of the flushing fluid from the flow chamber.

Thereby the volume flow rate of the flushing fluid and the volume flow rate of the suction channel can be adapted to the application, wherein the volume flow rate of the suction flow is at least as large as the volume flow rate of the flushing fluid and preferably larger. Preferably the volume flow rate of the suction flow and/or a suction power of the suction unit is/are adjusted such that no flushing fluid or only a minor portion of the flushing fluid exits through the end opening of the liner.

By means of the suction unit, also a suction power and/or a volume flow rate of the suction flow can be adjusted such that fumes or other gases that are created during the treatment of the tissue by means of the electrosurgical instrument are extracted via the end opening, the inlet opening and the suction channel.

During operation of the electrosurgical device a voltage potential is applied to the at least one electrode. Flushing fluid is conducted via the flushing channel into the flow chamber and at least a portion thereof is discharged via the inlet opening and the suction channel out of the flow chamber. During treatment of tissue, e.g. cutting or coagulation of tissue, a spark is created at the at least one electrode that emits light. The light spectrum is characteristic for the type of the treated tissue. The light can incident via the light inlet surface and can be further conducted by means of the light conducting device to the light analysis unit, such that an evaluation about the type of the treated tissue is possible in the light analysis unit. The result of the analysis can be indicated to the surgeon optically and/or acoustically and/or haptically.

The flushing fluid may be gaseous or liquid. For example, carbon dioxide or air or argon or any combination thereof can be used as flushing fluid. Particularly argon is suitable for endoscopic use of the instrument and carbon dioxide and/or air for the open surgical use of the instrument.

BRIEF DESCRIPTION OF THE DRAWINGS

Embodiments of the invention are derived from the dependent claims, the description and the drawings. In the following, embodiments of the invention are explained based on the attached drawings. The drawings comprise the following figures:

DETAILED DESCRIPTION

Figure 1:
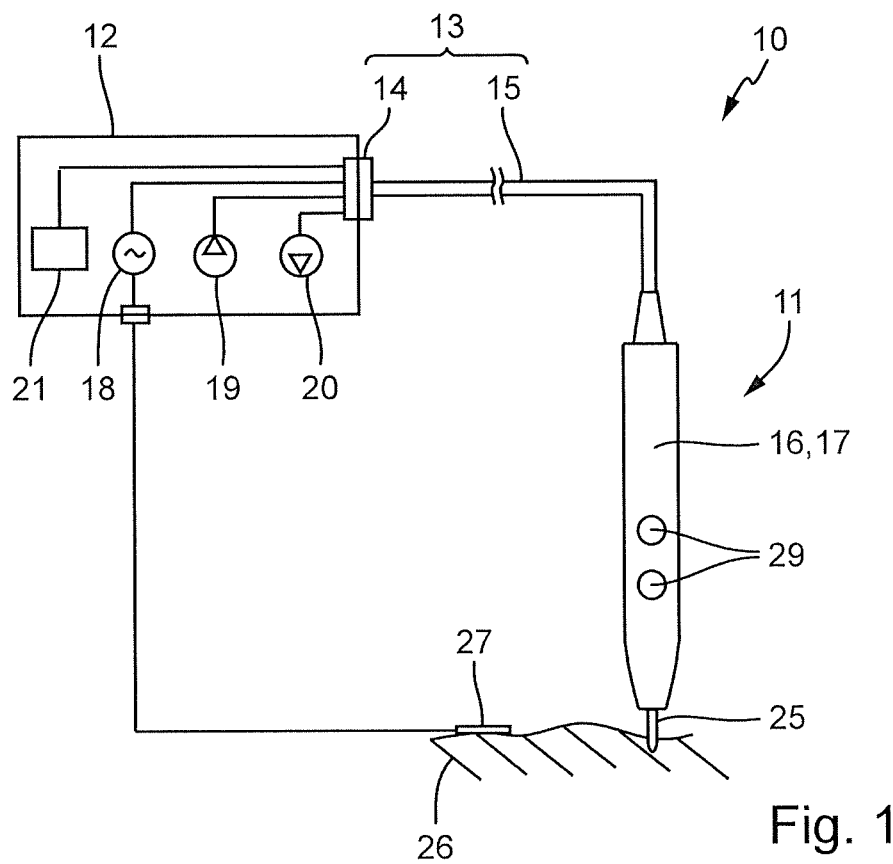
FIG. 1 a block diagram of an electrosurgical device comprising an electrosurgical instrument as well as a supply apparatus, FIG. 2 a perspective illustration of an embodiment of an electrosurgical instrument, FIGS. 3 and 4 an end section adjoining the distal end of the electrosurgical instrument of an embodiment of the electrosurgical instrument in a schematic cross-section illustration respectively, FIG. 5 an end section adjoining the distal end of the electrosurgical instrument of a modified embodiment, and FIG. 6 an end section adjoining the distal end of the electrosurgical instrument of a further embodiment of the electrosurgical instrument in a schematic cross-section illustration.

FIG. 1 illustrates an electrosurgical device 10 in the manner of a block diagram. The electrosurgical device 10 comprises an electrosurgical instrument 11 and a supply apparatus 12. The electrosurgical instrument 11 has a connection device 13 that is configured to establish an electrical and fluidical and in the embodiment illustrated here, in addition an optical connection between the electrosurgical instrument 11 and the supply apparatus 12. For this purpose the connection device can comprise at least one connection element 14 by means of which a preferably releasable connection can be established with the supply apparatus 12. The at least one connection element 14 can be a plug of the connection device 13, for example.

In the embodiment the connection device 13 comprises in addition multiple lines 15, wherein the lines 15 comprise fluidic lines, at least one electrical line and as an option at least one optical line. The lines 15 extend from the at least one connection element 14 into a liner 17 of the electrosurgical instrument 11. In the embodiment according to FIGS. 1-4, the liner 17 is formed by a housing 16.

In modification to the illustrated embodiment also multiple separate connection elements 14 can be present, e.g. a connection element 14 for connection of the fluidic lines 15, a connection element 14 for connection of the at least one electrical line and as an option, a connection element 14 for connection of an optical line 15.

The supply apparatus 12 is configured to supply fluids necessary for the operation of the electrosurgical instrument 11, to supply electrical energy for the operation and to discharge fluids. For this purpose in the embodiment the supply apparatus 12 comprises a voltage source 18 by means of which an electrical voltage can be provided, particularly a radio frequency alternating voltage. The supply apparatus 12 has in addition a flushing fluid source 19 for supply of the electrosurgical instrument with a flushing fluid as well as a suction unit 20. By means of the suction unit 20, fluids can be discharged from the distal end section of the electrosurgical instrument 11.

In addition the electrosurgical device 10 comprises a light analysis unit 21 that is arranged outside of housing 16 of the electrosurgical instrument 11 in the embodiment. It can be part of the supply apparatus 12, as illustrated in FIG. 1. As an alternative thereto, the light analysis unit 21 can also be arranged outside of supply apparatus 12 as separate unit.

The electrosurgical instrument 11 has at least one electrode 25 that is electrically connected with the connection device 13. A voltage potential and particularly a radio frequency alternating voltage potential can be applied to the electrode 25 via the connection device 13 by means of the voltage source 18. FIG. 1 illustrates an embodiment of the electrosurgical instrument 11 in form of a monopolar instrument that comprises only one electrode 25. In order to close a current circuit during treatment of biological tissue 26 by means of the electrosurgical instrument 11, a separate counter electrode 27 is electrically connected to the supply apparatus 12 and particularly the voltage source 18 in order to be able to obtain a closed current circuit via the biological tissue 26 to be treated. For this purpose the counter electrode 27 can be attached to the patient.

In modification to the embodiment illustrated in FIG. 1, the electrosurgical instrument 11 can also be configured as bipolar or multi-polar instrument having at least two electrodes 25 such that a separate counter electrode 27 can be omitted. The current circuit can then be closed via the at least two electrodes 25 of the electrosurgical instrument 11 and via the biological tissue 26 to be treated.

In the embodiment illustrated in FIGS. 1-4 the electrosurgical instrument 11 is equipped with a handle 28 by means of which a surgeon holds or guides the electrosurgical instrument 11. The handle 28 can be formed by a part of the housing 16, as in the embodiment, or can be attached to the housing 16. In the proximity of the handle 28, in addition at least one operation element 29 can be provided on the housing 16, e.g. in order to control the supply apparatus 12. By means of the at least one operation element 29, a desired voltage potential can be applied to the electrode 25 and/or the supply of a flushing fluid by means of the flushing fluid source 19 can be controlled and/or the suction by means of the suction unit 20 can be controlled, for example.

The liner 17 and, according to the example the housing 16, has an end opening 30 at its distal end. In the embodiment according to FIGS. 1-4 the at least one electrode 25 extends beyond the distal end of the housing 16 or the liner 17 in a longitudinal direction L and can extend through the end opening 30. The longitudinal direction L is particularly defined by the direction in which the electrode 25 extends originating from its distal end and/or the direction in which the longitudinal axis of the liner 17 or the housing 16 extends. In the embodiment the longitudinal direction L is orientated orthogonal to a plane in which the end opening 30 extends.

Figure 2:
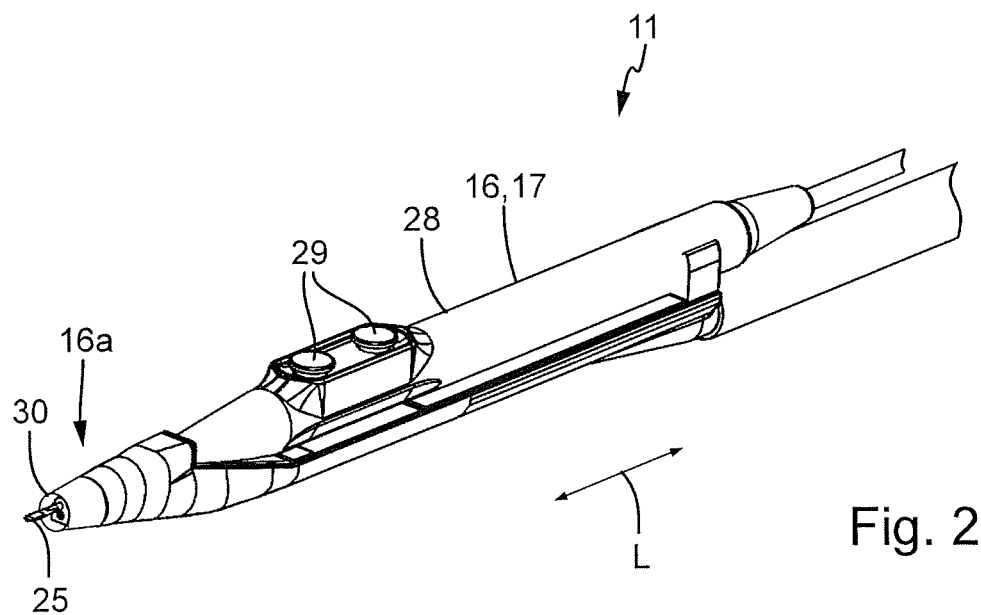

As illustrated in FIG. 2, the housing 16 can consist of multiple-assembled parts. As an alternative thereto, the housing 16 can also be monolithic.

Figure 3:
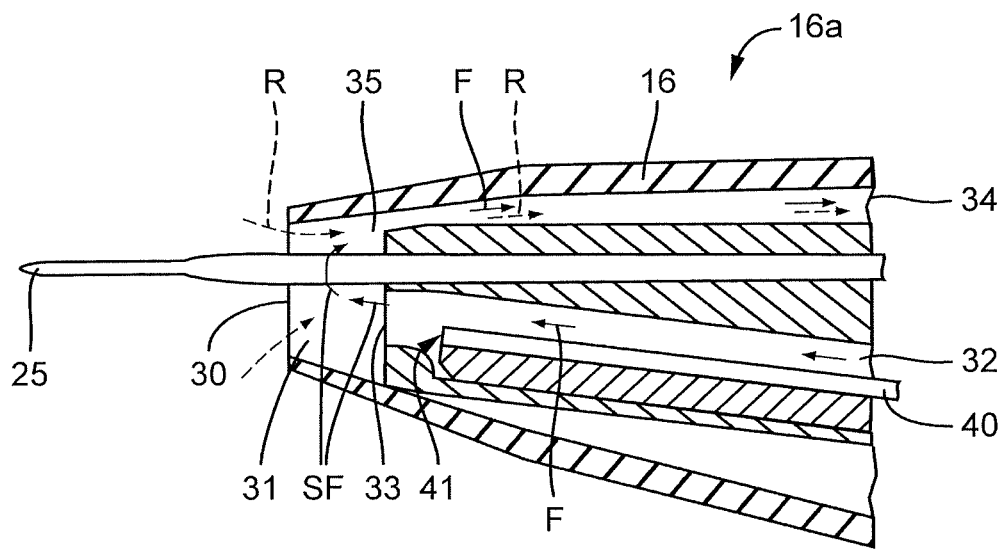
Figure 4:
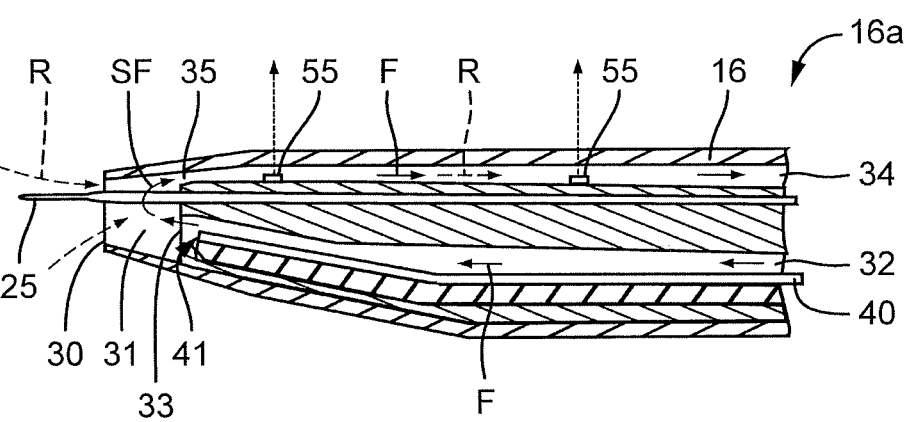

The distal end section 16a of the housing 16 adjoining the end opening 30 is illustrated in FIGS. 3 and 4 in an enlarged manner in a schematic cross-section. The housing 16 limits a flow chamber 31 directly adjacent to the end opening 30 provided at the distal end. A flushing channel 32 that extends preferably inside the housing 16 or the liner 17 has an exit opening 33 that directly adjoins the flow chamber 31. The flushing channel 32 thus opens out into the flow chamber 31 at the exit opening 33. Flushing fluid F exiting the exit opening 33 creates a flushing fluid flow SF in the flow chamber 31.

The exit opening 33 and/or the section of the flushing channel 32 adjoining thereto are, according to the example, orientated by an acute angle in relation to the longitudinal direction L. The main flow direction of the flushing fluid flow SF adjacent to the exit opening 32 corresponds, according to the example, to a longitudinal center axis of the section of the flushing channel 32 adjoining the exit opening 33 that can be orientated relative to the longitudinal direction L by an angle of, for example, maximum 30° or maximum 20° or maximum 10°. In other embodiments the main flow direction can also be orientated parallel to the longitudinal direction L.

In addition, the electrosurgical instrument 11 has a suction channel 34 that directly opens out into the flow chamber 31 via an inlet opening 35. Fluid can be discharged from the flow chamber 31 via the suction channel 34, particularly flushing fluid F. In addition, fumes R that are created during the treatment of biological tissue 26, can be extracted by suction via the suction channel 34. Such fumes R can be sucked into the flow chamber 31 via the end opening 30 and can enter the suction channel 34 via the inlet opening 35.

In the embodiment the electrode 25 is arranged between the exit opening 33 of the flushing channel 32 and the inlet opening 35 of the suction channel 34 with view orthogonal to the longitudinal direction.

In operational condition of the electrosurgical instrument 11 suction channel 34 is fluidically connected with the suction unit 20 and flushing channel 32 is fluidically connected with the flushing fluid source 19. In addition, an electrical connection is established between voltage source 18 and electrode 25.

The electrosurgical instrument also comprises a light conducting device 40 that comprises a light inlet surface 41 that faces the flow chamber 31 or the at least one electrode 25. The light conducting device 40 can be formed, for example, by an optical fiber, such as a glass fiber. The light inlet surface 41 can be formed by the face of the optical fiber.

As an alternative thereto, the optical fiber can be coupled with an optic, e.g. a lens, provided at the light inlet surface 41.

The light inlet surface 41 is orientated such that it can receive light that is emitted due to spark creation during processing of biological tissue 26. This light is further guided via the light conducting device 40 to the light analysis unit 21 for evaluation, particularly spectral analysis. In doing so, the type of treated tissue can be extrapolated.

The light inlet surface 41 is sensitive to contamination. By means of flushing fluid F supplied into the flow chamber 31, contamination of the light inlet surface 41 can be avoided or at least mitigated. For example, tissue particles, fume particles, tissue liquid or the like may reach the light inlet surface 41 and may be collected there. It has shown that the protection of the light inlet surface 41 from contamination can be improved, if the flushing fluid F remains at least substantially within the flow chamber 31 and does not or does only to a minor portion exit from the end opening 30. By impingement of flushing fluid F on tissue 26 contamination particles may be thrown through the end opening 30 on the light inlet surface 41. Due to reducing the portion of the flushing fluid F impinging on biological tissue 26, the danger of such a contamination of the light inlet surface 41 is reduced.

For this reason, in the configuration of the electrosurgical instrument 11 a flow chamber 31 is formed inside the liner 17 or the housing 16 such that flushing fluid F can be discharged via the suction channel 34 before it leaves the liner 17 or the housing 16. It is advantageous, if substantially all of the flushing fluid F is discharged via the suction channel 34 that is supplied via the flushing channel 32 in the flow chamber 31. As explained, in addition also fumes R can be conveyed via the suction channel 34 away from the treatment location.

For protection of the light inlet surface 41, flushing fluid F surrounds the light inlet surface 41 and particularly the section of the light conducting device 40 adjoining thereto, particularly before flushing fluid F exits into the flow chamber 31 at the exit opening 33. For this purpose the distal end section of the light conducting device 40 adjoining the light inlet surface 41 is arranged directly adjacent to the flushing channel 32 or inside the flushing channel 32, as e.g. illustrated in FIGS. 3 and 4. Thereby it is advantageous, if the light inlet surface 41 has a larger distance to the end opening 30 in longitudinal direction L than the exit opening 33.

It is also preferred, if the exit opening 33 comprises a distance in longitudinal direction L to the distally arranged end opening 30 that is at least as large as the distance between the inlet opening 35 of the suction channel 34 and the end opening 30 in longitudinal direction. By means of this arrangement, extraction by suction of flushing fluid F from the flow chamber 31 is simplified or improved.

During operation of the electrosurgical instrument 11 the mass or volume flow rate supplied to the flow chamber 31 by means of the flushing fluid source 19 via the flushing channel 32 is at most as large as the mass or volume flow rate of the flow into the suction channel 34 that is adjusted by means of the suction unit 20. Preferably the mass or volume flow rate of the flow into the suction channel 34 is larger than the mass or volume flow rate into the flushing channel 32.

The embodiment of the electrosurgical instrument 11 described so far is particularly configured for open surgical use. A modified embodiment of the electrosurgical instrument is shown in FIG. 5 that is particularly suitable also for laparoscopic interventions or interventions with a flexible endoscope or minimally invasive surgical interventions.

Figure 5:
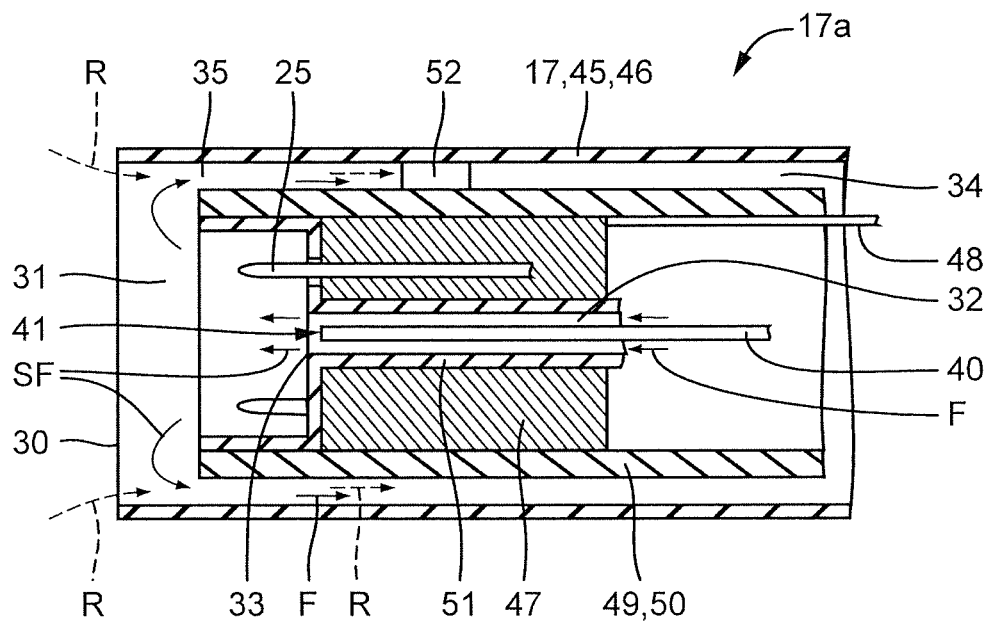

FIG. 5 shows a schematic cross-section of a distal end section 17a of a liner 17 of the electrosurgical instrument. In this embodiment the liner 17 is formed by a flexible hose 45 or a rigid tube 46. The liner 17 can also be configured as flexible hose 45 in at least one section and as rigid tube 46 in at least one section. In the embodiment the liner 17 has a hollow cylindrical shape, at least in the distal end section 17a.

Inside the liner 17 an electrode support 47 is arranged that is electrically connected with at least one electrode 25 and an electrical conductor 48. The electrical conductor 48 extends inside the liner 17 and is electrically connected with the connection device 13. In the embodiment the electrode support 47 is arranged inside an inner hose 49 or an inner tube 50. Adapted to the liner 17 a flexible inner hose 49 or a rigid inner tube 50 can be selected.

The flushing channel 32 extends through the inner hose 49 or the inner tube 50 that extends, for example, along the longitudinal axis of the liner 17. In this embodiment the light conducting device 40 and the light inlet surface 41 are arranged inside the flushing channel 32. In the area of the distal end of the flushing channel 32 the electrode support 47 is arranged adjacent to the flushing channel 32 that can, for example, surround the flushing channel 32 coaxially. Between the electrode support 47 and the flushing channel 32 a thermal barrier can be provided that is, for example, part of a barrier element 51. A first section of the barrier element 51 surrounds the distal end section of the flushing channel 32 coaxially and forms the exit opening 33 according to the example. Adjoining this first section extending coaxially to the flushing channel 32 the barrier element 51 comprises a cup-shaped second section that is arranged inside the flow chamber 31.

Originating from the electrode support 47 the at least one electrode 25 extends through the barrier element 51 into the interior of the cup-shaped second section of the barrier element 51. The at least one electrode 25 ends with its distal end preferably inside the second section of the barrier element 51. The distal end of the barrier element 51 is, according to the example, on the same level as the distal end of the inner hose 49 or the inner tube 50. The distal end of the inner hose 49 or the inner tube 50 and/or the distal end of the barrier element 51 are arranged with distance in longitudinal direction L to the distally arranged end opening 30 inside the liner 17 according to the example.

The suction channel 34 is, according to the example, formed by a radial distance between the inner hose 49 or the inner tube 50 on one side and the liner 17 (hose 45 or tube 46). Preferably multiple spacers 52 are arranged in the suction channel 34 distributed in circumferential direction in order to define the relative position between the inner hose 49 or the inner tube 50 on one hand and the liner 17 on the other hand. The inner hose 49 or the inner tube 50 can be arranged coaxially at least in sections and/or in a non-coaxial manner, at least in sections with regard to one another. The flow through the suction channel 34 can pass the spacers 52. The dimension and/or shape and/or position and/or surface characteristic of one or more or all of the spacers 52 can be selected in order to influence a flow characteristic of the flow through the suction channel 34. For example, the volume flow rate through the suction channel 34 can be specifically adjusted or choked.

Also in the embodiment according to FIG. 5 the inlet opening 35 of the suction channel 34 and the exit opening 33 of the flushing channel 32 are arranged inside the liner 17 and with distance to the end opening 30 of the liner 17 in longitudinal direction L. As apparent from FIG. 5, the distance between the exit opening 33 and the end opening 30 is larger than the distance between the inlet opening 35 and the end opening 30.

The above-described embodiments of the electrosurgical instrument 11 or the electrosurgical device 10 operate during the treatment of biological tissue 26 as follows:

The electrosurgical instrument 11 is connected to the supply apparatus 12 by means of the connection device 13. If necessary, the counter electrode 27 is attached to the patient and also connected with the supply apparatus 12. As explained, a separate counter electrode 27 is not necessary in bipolar electrosurgical instruments 11.

By means of the at least one operation element 29 the surgeon controls the operation of the electrosurgical instrument 11 and e.g. the application of an alternating voltage potential to the at least one electrode 25 in order to treat, e.g. cut or seal, biological tissue 26. Thereby sparks are created at the electrode 25, the light of which enters the light inlet surface 41 and is further conducted via the light conducting device 40 to the light analysis unit 21. The light analysis unit 21 is configured to analyze the received light, particularly by means of a spectral analysis, in order to determine the type of tissue 26 that is actually treated by means of the electrosurgical instrument 11.

During this treatment flushing fluid F is introduced in the flushing channel 32 by means of the flushing fluid source 19 and flows there via the exit opening 33 into the flow chamber 31. Adjacent to the exit opening 33, a flushing fluid flow SF forms in the flow chamber 31. In the embodiment the major portion and particularly at least 75% or at least 80% or at least 90% and further preferably all of the flushing fluid F that flows into the flow chamber 31 is discharged via the suction channel 34 from flow chamber 31. At most a minor portion of the flushing fluid F may leave the flow chamber 31 through the end opening 30. Preferably no flushing fluid F exits through end opening 30. The extraction by suction of the flushing fluid F from flow chamber 31 is carried out by means of the suction unit 20 that adjusts a correspondingly large volume flow rate or partial vacuum and thus respectively large suction power in order to obtain the desired effect. Fumes R created during the treatment of tissue 26 are also distracted by suction through the end opening 30 and the inlet opening 35 into the suction channel 34 and are discharged.

In all of the embodiments at least one sensor 55 can be arranged in the suction channel 34. The at least one sensor 55 is preferably electrically connected with a connection device 13, such that an electrical sensor signal can be transmitted via the connection device 13 to the supply apparatus 12. The at least one sensor 55 is configured to detect a parameter of the flow inside the suction channel 34, such as a pressure, a flow velocity, a volume flow rate, etc. For the measurement of different parameters, multiple different sensors 55 can be provided. In this embodiment the possibility exists to control the suction unit 20 based on desired values for the at least one flow parameter in a closed loop.

Figure 6:
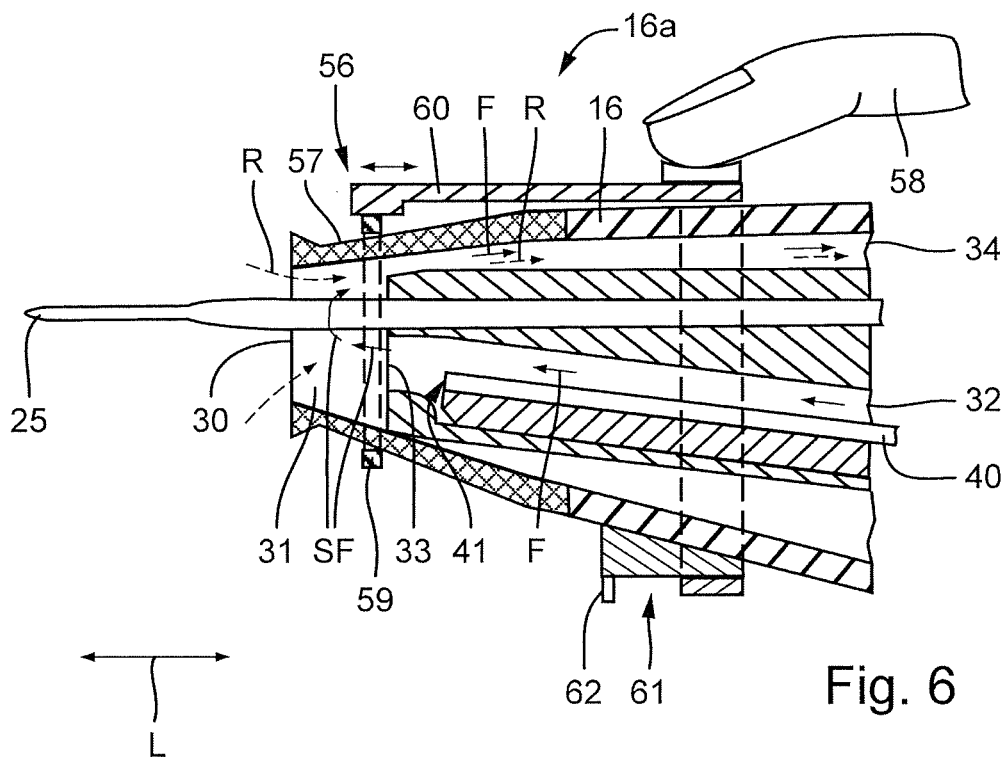

In FIG. 6 a distal end section 16a of another modified embodiment of the electrosurgical instrument 11 is illustrated. The electrosurgical instrument 11 is configured in a similar manner as the embodiment according to FIGS. 3 and 4. In the following the differences with regard to the embodiments of FIGS. 3 and 4 are explained and apart therefrom reference is made to the description above.

Different to the first embodiment according to FIGS. 3 and 4, the housing 16 has a distal end section 16a in which an area 57 having a cross-section that can be modified by means of an adjustment device 56 directly adjoins the end opening 30. The area 57 of the end section 16a of the housing 16 can consist, for example, of a flexible or elastic material that can be elastically deformed under influence of the adjustment device 56. Thereby the flow cross-section of the end opening 30 as well as the flow cross-section inside the area 57 can be adjusted by means of the adjustment device 56. The adjustment device 56 can be manually actuated according to the example, e.g. by means of a finger 58.

An adjustment ring 59 that is movably supported in longitudinal direction L surrounding the area 57 is part of the adjustment device 56. The area 57 comprises a non-constant outer diameter and/or a non-constant outer circumference. The position of the adjustment ring 59 relative to the area 57 defines the outer circumference thereof at this location. In doing so, in turn the inner cross-section of the area 57 and thus the flow cross-section as well as the cross-section of the end opening 30 is defined. In other words, the area 57 of the distal end section 16a gets larger or smaller with view radial to the longitudinal direction L depending on the relative position between the adjustment ring 59 and the area 57 in longitudinal direction L.

In the embodiment the adjustment ring 59 is arranged on a carrier 60 that is movably supported in longitudinal direction L on the housing 16. For example, the carrier 60 can be arranged movably in longitudinal direction L on a cylindrical support part 61. The support part 61 can at least partly be formed by the housing 16 and/or by additional components connected with the housing 16. At least a part of the carrier 60 can surround the support part 61 in circumferential direction around the longitudinal direction L partly or completely.

In direction toward the distal end a stop 62 can be provided on the support part 61 in order to limit the movement of the carrier 60 in longitudinal direction and thus the movement of the adjustment ring 59 in longitudinal direction L. In the embodiment one single stop 62 is provided that limits the movement of the carrier 60 and the adjustment ring 59 in the distal direction. In addition or as an alternative a further stop can be provided that limits the movement in proximal direction, if necessary. The movement in proximal direction is limited in the embodiment illustrated in FIG. 6, in that the area 57 transitions at a location in a non-deformable, particularly non-elastic part of the housing 16, such that the adjustment ring 59 can be moved at most up to the non-deformable part of the housing 16.

Embodiments of the invention refer to an electrosurgical instrument 11 that can be connected to a supply apparatus 12 for operation. The electrosurgical instrument 11 has an end opening 30 at the distal end and supports at least one electrode 25 in the area of the end opening 30 to which an alternating voltage potential can be applied. Directly adjoining the end opening 30, a liner 17 of the electrosurgical instrument 11 limits a flow chamber 31 inside the liner 17. With distance to the end opening 30 a flushing channel 32 opens out into the flow chamber 31 via an exit opening 33 and a suction channel 34 opens out into the flow chamber 31 via an inlet opening 35. A flushing fluid F can be introduced in the flow chamber 31 via the flushing channel 32 and can be extracted by suction via the suction channel 34. The major portion of the flushing fluid F flowing into the flow chamber 31 is discharged via the suction channel 34 from the flow chamber 31 and can thus not leave the flow chamber 31 via the end opening 30. In doing so, the light inlet surface 41 of a light conducting device 40 arranged inside the liner 17 can be effectively protected from contamination.

The invention claimed is:

1. An electrosurgical instrument comprising:
   a connection device configured to connect to a supply apparatus;
   a liner having a distal end opening arranged at a distal end of the liner;
   at least one electrode electrically connected with the connection device that is arranged adjacent to the distal end opening or that extends beyond the distal end opening in a longitudinal direction;
   a light conducting device that comprises a light inlet surface that is arranged inside the liner;
   a flushing channel fluidically connected with the connection device that comprises an exit opening that opens out into a flow chamber limited by the liner and that is arranged with distance to the distal end opening in longitudinal direction, such that a flushing fluid flowing through the flushing channel flows out of the exit opening and creates a flushing fluid flow in the flow chamber from the exit opening in direction toward the distal end opening; and
   a suction channel fluidically connected with the connection device that comprises an inlet opening opening out into the flow chamber and that is configured to receive at least a portion of the flushing fluid of the flushing fluid flow via the inlet opening and to discharge it from the flow chamber.

2. The electrosurgical instrument according to claim 1, wherein the inlet opening of the suction channel is arranged with distance to the distal end opening in longitudinal direction.

3. The electrosurgical instrument according to claim 1, wherein the inlet opening of the suction channel is arranged closer to the distal end opening than the exit opening of the flushing channel in longitudinal direction or wherein the inlet opening and the exit opening have equal distances to the distal end opening in longitudinal direction.

4. The electrosurgical instrument according to claim 1, wherein the flow chamber and/or the suction channel are dimensioned such that the flushing fluid flow does not exit from the distal end opening.

5. The electrosurgical instrument according to claim 1, wherein the light inlet surface of the light conducting device is further away from the distal end opening in longitudinal direction than the exit opening.

6. The electrosurgical instrument according to claim 1, wherein at least the distal end section of the light conducting device adjoining the light inlet surface is arranged inside the flushing channel.

7. The electrosurgical instrument according to claim 1, wherein at least one sensor electrically connected with the connection device is comprised in the suction channel and is configured to detect a pressure and/or a flow parameter inside the flushing channel.

8. The electrosurgical instrument according to claim 1, wherein the liner is part of a housing on which the connection device is arranged on the proximal end.

9. The electrosurgical instrument according to claim 1 that is configured as flexible endoscopic or laparoscopic instrument and the liner comprises a flexible hose and/or a rigid tube.

10. An electrosurgical device comprising the electrosurgical instrument according to claim 1 and a supply apparatus that is connected with the electrosurgical instrument by means of the connection device,
- wherein a light analysis unit is provided that is optically connected with the light conducting device and that is configured to carry out an analysis of the light received via the light inlet surface,
- wherein the supply apparatus comprises a voltage source that is electrically connected with the at least one electrode of the electrosurgical instrument in order to apply an electrical voltage potential to the at least one electrode,
- wherein the supply apparatus comprises a flushing fluid source that is fluidically connected with the flushing channel in order to supply flushing fluid to the flushing channel, and
- wherein the supply apparatus comprises a suction unit that is fluidically connected with the suction channel of the electrosurgical instrument in order to discharge at least a portion of flushing fluid of the flushing fluid flow from the flow chamber via the inlet opening and the suction channel.

11. The electrosurgical device according to claim 10, wherein the supply apparatus is configured to adjust a volume flow rate of the flushing fluid by means of the flushing fluid source and to adjust a volume flow rate of the suction flow by means of the suction unit, wherein the volume flow rate of the suction flow is at least as large as the volume flow rate of the flushing fluid.

12. The electrosurgical device according to claim 10, wherein the supply apparatus is configured to adjust a volume flow rate of the suction flow and/or a suction power by means of the suction unit such that no flushing fluid exits from the distal end opening of the liner.

13. The electrosurgical device according to claim 10, wherein the supply apparatus is configured to adjust a volume flow rate of the suction flow and/or a suction power by means of the suction unit that fumes created during treatment of tissue can be sucked through the distal end opening of the liner.

14. A method for operating the electrosurgical device according to claim 10, the method comprising:
- applying an electrical voltage potential to the at least one electrode of the electrosurgical instrument;
- supplying of a flushing fluid in the flushing channel and out of the exit opening into the flow chamber;
- receiving light through the light inlet surface and conducting the received light to the light analysis unit; and
- discharging at least a portion of the flushing fluid from the flow chamber via the suction channel.

* * * * *